United States Patent [19]

Benjaminson

[11] 4,261,849

[45] Apr. 14, 1981

[54] ANTI-MICROBIAL, DEODORIZING, CLEANING COMPOSITIONS

[76] Inventor: M. A. Benjaminson, 170 Broadway Suite 210, New York, N.Y. 10038

[21] Appl. No.: 69,503

[22] Filed: Aug. 24, 1979

[51] Int. Cl.$^3$ .......................... C11D 7/02; C11D 7/12
[52] U.S. Cl. ...................................... 252/106; 252/88; 252/89.1; 252/140; 252/160; 252/174.11; 252/174.24
[58] Field of Search ................. 252/88, 89.1, 145, 140, 252/160, 174.11, 174.25, 106

[56] References Cited

U.S. PATENT DOCUMENTS

| | | | |
|---|---|---|---|
| 839,290 | 12/1906 | Henderson | 252/160 |
| 1,118,209 | 11/1914 | Mattes | 252/89.1 |
| 1,278,411 | 9/1918 | Adler | 252/160 |
| 1,316,090 | 9/1918 | Tomashot | 252/160 |
| 1,449,388 | 3/1923 | Ferrell | 252/160 |
| 1,844,933 | 2/1932 | Cyganick | 252/160 |
| 2,480,753 | 8/1949 | McCarter | 252/174.25 |

FOREIGN PATENT DOCUMENTS 21190 of 1902 United Kingdom .
406746 8/1934 United Kingdom .

Primary Examiner—P. E. Willis, Jr.

[57] ABSTRACT

An anti-microbial, deodorizing and cleaning composition comprising a uniform admixture of particles of alkali metal bicarbonate, alkali metal chloride and fuller's earth in a ratio in parts by weight of alkali metal bicarbonate: alkali metal chloride: fuller's earth in parts by weight of about 0.25 to 0.45: about 0.35 to 0.55: about 0.15 to 0.25.

6 Claims, No Drawings

ANTI-MICROBIAL, DEODORIZING, CLEANING COMPOSITIONS

BACKGROUND OF THE INVENTION

1. Field of the Invention

This invention relates to anti-microbial, deodorizing cleaning compositions and to methods for using the compositions.

2. Brief Description of the Prior Art

Many commercially available products make claim to an effectiveness for removing odors and smells. Actually, most such products do not in fact remove such odors and smells but rather merely mask them, generally by using an essence or other additive which acts on the sensory nerve endings of the nasal mucosa. Other products are known which contain soaps or have a detergent action so as to remove grease or dirt. Still other compositions have been described which are characterized by their germicidal effectiveness. Each of these compositions is not without its drawbacks, however. For example, few if any such compositions are capable of cleaning, absorbing (e.g. oils, grease, water, dirt etc.), deodorizing and protecting against microbial activity. All compositions of this type generally fail in at least one of these respects and those that might approach these capabilities frequently have an adverse effect on the working surface, or a toxic effect on humans and animals, or otherwise suffer from a lack of efficiency.

OBJECTS OF THE INVENTION

Thus, one object of the invention is to remove the odor producing substances rather than merely masking the odors and smells.

Yet another object of the invention is to provide a nontoxic composition which cleanses surfaces by removing and absorbing oil, grease, dirt and the like in an efficient manner.

A further object of the invention is to provide a composition which is not irritating to the skin and which in fact protects the skin from the dehydrating activity that typifies many other hand-cleaners and leaves the skin area soft and smooth.

Another object of this invention is to provide a composition which in addition to possessing the aforementioned properties simultaneously protects the surface treated or cleansed from microbial degradation.

SUMMARY OF THE INVENTION

These and other objects of the invention are obtained by a composition comprising an uniform admixture of particles of alkali metal bicarbonate, alkali metal chloride and fuller's earth in a ratio in parts by weight of alkali metal bicarbonate: alkali metal chloride: fuller's earth of about 0.25 to 0.45: about 0.35 to 0.55: about 0.15 to 0.25.

The preferred alkali metal bicarbonate is sodium carbonate and the preferred alkali metal chloride is sodium chloride. The proportions in which the components of the composition are employed are important for proportions significantly beyond those set out above fail to achieve the desired results. Best results are obtained with a composition having proportions of alkali metal bicarbonate: alkali metal chloride: fuller's earth of 7:9:4 parts by weight.

A particularly unexpected feature of the present invention resides in the finding that the composition possesses antimicrobial activity. The composition of the invention reduces the growth of both bacteria and fungi. This discovery is surprising because none of the individual components of the composition are recognized as bactericides or fungicides. In combination, however, the components, for reasons not clearly understood, exhibit an anti-microbial inhibitory activity that contributes in a number of ways to the utility of the invention. For instance, not only does the composition of the invention remove odors by absorbing the odor-producing substance, its anti-microbial inhibitory activity protects against microbial biodegradation of the material or substrate worked on. Similarly, the anti-microbial inhibitory characteristics of the compositions of the invention renders unnecessary the use of preservatives or anti-rot agents whose preservative effect is based on the poisoning of an enzyme or a particular metabolic pathway. Preservatives of the latter type tend to be toxic and therefore undesirable.

Another advantage provided by the anti-microbial inhibitory activity of the composition of the invention resides in the fact it renders unnecessary use of scents and essences normally employed in absorbent compositions because of their inability to provide long-lasting deodorizing protection.

Preparation of the compositions of the invention is achieved by simply mixing together in the defined proportions of particles of each of the components to provide a dry uniform admixture. This is most conveniently accomplished by the use of a dry blender but any suitable mixing means can be employed. The particle size of the components can very widely depending on sieve sizes.

The compositions of the invention, in view of their extraordinary properties, find a variety of uses. These uses include, by way of illustration:

(1) deodorant, dessicant (cleaner) for carpets, rugs, upholstery, mattresses, foam rubber (removal of musty, food, urine and vomit odors)
(2) hand cleaner and emollient
(3) hygienic metal cleaner and polish
(4) hygienic kitchen cleanser (pots, pans enamel and hard rubber surfaces)
(5) mop and sponge sweetner
(6) refrigerator deodorizer and cleanser
(7) scavenger for recovery of oil and grease
(8) fire and smoke damage deodorizer
(9) preservative for long-term storage of rugs, carpets, mattresses and upholstered furniture
(10) vacuum cleaner bag freshener
(11) odor remover, veterinary (pet and other animals)
(12) air/air filter deodorizer
(13) mold and mildew preventative in the shipping of shoes, leather goods, rugs, carpets, upholstery and other materials (such as wood) subject to rot.
(14) garbage receptacle deodorizer The method of using the compositions of the invention will vary of course depending upon the application to which the composition is to be put.

In instances such as (1) to (5) above where the substrate or surface to be cleaned is dry, it is advantageous to at least wet the substrate or surface with water before applying the dry composition of the invention. The dry powdery composition of the invention can be applied by any means as by simply sprinkling the composition onto the wetted surface or substrate, brushed in for deep pile carpets, spread in other cases. For use (1) it is allowed to dry (overnight, if necessary) and vacuumed up. For use (2), (3) and (4) it is rinsed off with water until entirely removed.

For use (6) above, the powder of composition of the invention is advantageously kept in the open (perforated) container in the refrigerator during shipping. By the time the destination is reached, the food odor should be removed or substantially reduced. It is then spread over the interior of the refrigerator with a moist sponge and rinsed off with water until no film remains.

For use (7), the powder of the invention is dispensed over the surface of the spill until the oil and/or grease is absorbed. The composition of the absorbed oil or grease is then removed by scooping up and the process is repeated as often as needed.

For use (8) above, the powder composition of the invention is spread throughout the room or rooms on all surfaces including furnishings and damped and wet areas. Whether the part of composition is removed and whether a treatment is necessary depends on the severity of the conditions.

For use (9) above, the powder composition of the invention is spread on the rug, roll and wrap surface and when the rug is to be plugged into use, the powder composition is vacuumed up. Mattresses and upholstered furniture should be treated similarly.

For use (10) above, the powder composition of the invention is shaken into a permanent vacuum cleaner bag and the vacuum used in a normal manner.

For use (11) above, the powder composition is shaken into cat litter until the wet spots are covered. This procedure can be repeated until the litter is saturated with urine and then the litter is discarded. On rugs, etc. and where pets have sat, slept, urinated, etc., treatment with the compositions of the invention is as described above with reference to rugs or upholstery.

For use (12) above, the composition of the invention is fixed in any suitable manner to a suitable filter material.

For use (13) above, the same procedure as described above with reference to use (9) on rugs, rolls and wraps is employed.

For use (14) above, the powder composition of the invention is shaken into the interior of garbage receptacles until a deodorizing effect is noted. The powder composition can be used to cleanse and sanitize, as well, as by adding water to make a paste and scrubbing the receptacle with an appropriate cleaning device.

The following examples are included to further illustrate the present invention.

EXAMPLE I

Seven parts by weight sodium bicarbonate (USP powder), nine parts by weight sodium chloride (food grade table salt) and four part by weight fuller's earth (90–100 mesh) are added to a dry blender and mixed until a uniform homogeneous admixture is obtained.

The following example is included to demonstrate the fungistatic and bacteriostatic activity of the compositions of the invention.

EXAMPLE II

A. Fungistatic Activity:
Test Method
One gram of the composition of Example I is mixed six drops of water to yield a paste. The paste is spread onto a 4.5 cm diameter Whatman No. 1 filter paper disc. The coated side of the filter paper is placed in intimate contact to the surface of a Sabouraud Dextrose Agar plate which has been inoculated with a slurry of spores of the mildew fungus, *Aspergillus niger* immediately before application of the composition coated filter paper. The test specimen is incubated for 7 days at 28° C. and the growth pattern observed.
Test Results
A 20 mm growth-free zone was observed around the treated filter paper (coated with a paste of the composition)
Remarks
The results indicate a marked inhibitory effect on the growth of the mildew fungus.

B. Bacteriostatic Activity:
Test Method
One gram of each of the following products was tested for bacteriostatic activity: The powder composition of Example I, Airwick Carpet Fresh, Dusto Fresh Floors. Sisal contaminated with bacteria was prepared in three 3 gram samples. The contaminated sisal samples were distributed in separate plastic bags. One gram of composition of Example I was placed in a bag of contaminated sisal and the contents vigorously shaken. The same procedure was followed for the other two products. Then, for each product individually, one 0.1 gram portion was placed in a test tube containing 10 ml of sterile distilled water and then shaken. Serial dilutions were made and then plated onto Nutrient Agar. After incubation at 25° C. for 24 hours, the number of colony forming units was determined.
Test Results
Composition Example I: $4 \times 10^4$ bacteria/ml
Airwick: $8 \times 10^4$ bacteria/ml
Dusto: $6 \times 10^4$ bacteria/ml
Remarks
The composition of Example I shows significant inhibition of the growth of bacteria and is several fold more effective as an antibacterial than the other products tested.

It is claimed:

1. A microbial, deodorizing and cleaning composition consisting essentially of a uniform admixture of particles of alkali metal bicarbonate, alkali metal chloride and fuller's earth in a ratio in parts by weight of alkali metal bicarbonate: alkali metal chloride: fuller's earth in parts by weight of about 0.25 to 0.45: about 0.35 to 0.55: about 0.15 to 0.25.

2. A composition according to claim 1 wherein the alkali metal chloride is sodium chloride.

3. A composition according to claim 1 wherein the alkali metal bicarbonate is sodium bicarbonate.

4. A composition according to claim 1 which the alkali metal chloride is sodium chloride and the alkali metal bicarbonate is sodium bicarbonate.

5. A composition according to claim 1 wherein the weight ratio of alkali metal bicarbonate: alkali metal chloride: fuller's earth in parts by weight is 7:9:4.

6. A composition according to claim 5 wherein the alkali metal bicarbonate is sodium bicarbonate and the alkali metal chloride is sodium chloride.

* * * * *